US012733977B2

(12) United States Patent
Cheng et al.

(10) Patent No.: US 12,733,977 B2
(45) Date of Patent: Sep. 15, 2026

(54) IMPACT-DURING-SUCTION SURGICAL URETEROSCOPE

(71) Applicants: NINGBO XINWELL MEDICAL TECHNOLOGY CO., LTD., Cixi (CN); THE FIRST AFFILIATED HOSPITAL OF NINGBO UNIVERSITY, Ningbo (CN)

(72) Inventors: Yue Cheng, Ningbo (CN); Jian Shan, Cixi (CN); Qingye Chen, Cixi (CN); Hailiang Wu, Cixi (CN); Li Fang, Ningbo (CN); Junjun Huang, Cixi (CN); Guohai Xie, Ningbo (CN)

(73) Assignees: NINGBO XINWELL MEDICAL TECHNOLOGY CO., LTD., Zhejiang (CN); THE FIRST AFFILIATED HOSPITAL OF NINGBO UNIVERSITY, Zhejiang (CN)

( * ) Notice: Subject to any disclaimer, the term of this patent is extended or adjusted under 35 U.S.C. 154(b) by 289 days.

(21) Appl. No.: 18/693,869

(22) PCT Filed: Sep. 8, 2022

(86) PCT No.: PCT/CN2022/117841
§ 371 (c)(1),
(2) Date: Mar. 20, 2024

(87) PCT Pub. No.: WO2023/045770
PCT Pub. Date: Mar. 30, 2023

(65) Prior Publication Data

US 2024/0382257 A1 Nov. 21, 2024

(30) Foreign Application Priority Data

Sep. 22, 2021 (CN) ......................... 202111096813.1

(51) Int. Cl.
*A61B 18/24* (2006.01)
*A61B 1/307* (2006.01)
(Continued)

(52) U.S. Cl.
CPC .............. *A61B 18/24* (2013.01); *A61B 1/307* (2013.01); *A61B 17/320016* (2013.01);
(Continued)

(58) Field of Classification Search
CPC ......... A61B 1/005; A61B 1/015; A61B 1/018; A61B 1/307; A61B 17/320016;
(Continued)

(56) References Cited

U.S. PATENT DOCUMENTS

2002/0002366 A1 1/2002 Grasso, III et al.
2006/0069343 A1* 3/2006 Rontal .................. A61B 17/24 604/20

(Continued)

FOREIGN PATENT DOCUMENTS

CN 208259737 U 12/2018
CN 112153929 A 12/2020

(Continued)

OTHER PUBLICATIONS

Notice of Reasons for Refusal issued for Japanese Patent Application No. 2024-518614, Dispatch date: Feb. 18, 2025, 8 pages including English machine translation.

(Continued)

*Primary Examiner* — Jocelin C Tanner
(74) *Attorney, Agent, or Firm* — HSML P.C.

(57) ABSTRACT

Disclosed is an impact-during-suction surgical ureteroscope, comprising: a ureteroscope main body, an operating portion operably arranged in the ureteroscope main body, and a lithotripter. The ureteroscope main body comprises a ureteroscope structure main body and a suction channel extend- (Continued)

ing from a front end to a rear end in the ureteroscope structure main body. The suction channel has a suction opening at the front end. The lithotripter is movably disposed in the ureteroscope structure main body so as to switch between a first state and a second state. When in the first state, a cutting head of the lithotripter extends out of the suction opening so as to impact a stone; when in the second state, the cutting head of the lithotripter is retracted into the suction opening and is used to impact crushed stones blocking the suction opening.

11 Claims, 11 Drawing Sheets

(51) Int. Cl.
*A61B 17/32* (2006.01)
*A61B 18/00* (2006.01)
*A61B 18/26* (2006.01)

(52) U.S. Cl.
CPC ............... *A61B 2018/00511* (2013.01); *A61B 2018/00982* (2013.01); *A61B 2018/263* (2013.01); *A61B 2218/007* (2013.01)

(58) Field of Classification Search
CPC .................... A61B 18/24; A61B 18/26; A61B 2018/00511; A61B 2018/00982; A61B 2018/263; A61B 2218/007
USPC .......................................................... 606/128
See application file for complete search history.

(56) References Cited

U.S. PATENT DOCUMENTS

2006/0173244 A1 8/2006 Boulais et al.
2010/0240950 A1 9/2010 Heimberger
2011/0105838 A1 5/2011 Fogel
2014/0275762 A1 9/2014 Irby, III
2016/0166320 A1* 6/2016 Ciulla .................... A61B 18/26 606/14
2022/0053998 A1* 2/2022 Ghani .................... A61B 18/26

FOREIGN PATENT DOCUMENTS

| | | | |
|---|---|---|---|
| CN | 212490057 | U | 2/2021 |
| CN | 213488692 | U | 6/2021 |
| CN | 213488693 | U | 6/2021 |
| CN | 113316428 | A | 8/2021 |
| CN | 213963295 | U | 8/2021 |
| EP | 4406471 | A1 | 7/2024 |
| JP | 2002537017 | A | 11/2002 |
| JP | 2016067702 | A | 5/2016 |
| WO | 2020150713 | A2 | 7/2020 |
| WO | 2021190669 | A1 | 9/2021 |

OTHER PUBLICATIONS

First Office Action issued for Chinese Patent Application No. 202111096813.1, dated Oct. 17, 2024, 10 pages including English machine translation.
International Search Report issued for International Patent Application No. PCT/CN2022/117841, Date of mailing: Oct. 28, 2022, 6 pages including English translation.
Written Opinion issued for International Patent Application No. PCT/CN2022/117841, Date of mailing: Oct. 28, 2022, 5 pages including English machine translation.
Extended European Search Report issue for European Patent Application No. 22871818.5, dated Aug. 20, 2025, 8 pages.
Decision to Grant a Patent issued for Japanese Patent Application No. 2024-518614, Dispatch date: Apr. 14, 2026, 5 pages including English machine translation.

* cited by examiner

IMPACT-DURING-SUCTION SURGICAL URETEROSCOPE

CROSS-REFERENCE TO RELATED APPLICATIONS

This application is an U.S. national phase application under 35 U.S.C. § 371 based upon international patent application No. PCT/CN2022/117841, filed on Sep. 8, 2022, which itself claims priority to Chinese patent application No. 2021110968131 filed on Sep. 22, 2021. The contents of the above identified applications are hereby incorporated herein in their entireties by reference.

TECHNICAL FIELD

The present application relates to the field of medical devices, and in particular to a break-during-suction type surgical ureteroscope.

BACKGROUND

In recent years, ureteroscopes have been widely used in the treatment of urinary calculi. Specifically, the ureteroscope can extend from the urethral orifice into the ureter or kidney, and medical workers can use the ureteroscope to cooperate with image acquisition equipment, lighting equipment, etc., to observe the situation in the kidney and crush the calculus at a target position.

In practical operation, during the process of breaking calculus through the ureteroscope, when a size of the calculus is large, it is difficult to pulverize the calculus after the calculus is crushed to a crushed calculus with equivalent diameter of 2 mm by conventional ureteroscope, and it is also difficult to expel the crushed calculus out of the patient's body through an effective discharging mechanism. As a result, 60%-90% of the crushed calculus remain in the kidney after the calculus are crushed by conventional ureteroscope and are difficult to be discharged from the body in time by natural excretion, which results in a low discharging rate of the crushed calculus. Residual crushed calculus may form a calculus street in the ureter to block the ureter, and residual crushed calculus is one of the main causes of high recurrence rate of calculus.

In order to solve this problem, a solution of a ureteroscope capable of discharging crushed calculus is provided. In the solution, the ureteroscope is provided with a crushed calculus discharging mechanism to discharge the crushed calculus out of the body in time. However, during practical operation, the crushed calculus is easily blocked in the discharging mechanism of the ureteroscope and is difficult to be discharged from the patient's body.

Therefore, there is a need for a new calculus discharging solution to avoid blockage during the process of discharging crushed calculus.

SUMMARY

An advantage of the present application is to provide a break-during-suction type surgical ureteroscope, which can prevent crushed calculus from being blocked at a suction opening in a break-during-suction type manner.

Another advantage of the present application is to provide a break-during-suction type surgical ureteroscope, a lithotripter of the break-during-suction type surgical ureteroscope is not only capable of breaking calculus formed in the kidney, but also capable of breaking calculus located at a suction opening of the suction channel configured to discharge crushed calculus, so as to prevent crushed calculus from blocking the suction opening.

Another advantage of the present application is to provide a break-during-suction type surgical ureteroscope, which can relatively quickly discharge crushed calculus to improve the calculus discharging efficiency.

Yet another advantage of the present application is to provide a break-during-suction type surgical ureteroscope, when a crushed calculus is stuck at a suction opening, a lithotripter also located at the suction opening can accurately break the crushed calculus.

Yet another advantage of the present application is to provide a break-during-suction type surgical ureteroscope, when a crushed calculus is stuck at a suction mouth, a position of the crushed calculus is relatively stable, and the lithotripter located at the suction opening is easier to crush the crushed calculus.

Yet another advantage of the present application is to provide a break-during-suction type surgical ureteroscope, through a reasonable arrangement of a perfusion opening of a perfusion channel and a suction opening, the design flexibility of the suction opening and the perfusion opening is relatively improved, and sizes of the suction opening and the perfusion opening can be relatively increase so that a crushed calculus can pass more easily to prevent the crushed calculus from blocking the break-during-suction type surgical ureteroscope.

Other advantages and features of the present application will become apparent from the following description, and may be realized by the means and combination specified in the claims.

In order to achieve the above-mentioned at least one advantage, according to an aspect of the present application, the present application provides a break-during-suction type surgical ureteroscope, including:

- a ureteroscope main body having a front end portion and a rear end portion, an operating portion operably coupled to the rear end portion of the ureteroscope main body, and a lithotripter;
- the ureteroscope main body includes a tube structure body, at least one perfusion channel in the tube structure body extending from the rear end portion to the front end portion, the at least one perfusion channel is provided with at least one perfusion opening located at the front end portion; and a suction channel in the tube structure body extending from the front end portion to the rear end portion, the suction channel is provided with a suction opening located at the front end portion;
- the lithotripter is movably provided in the tube structure body and is capable of switching between a first state and a second state, when in the first state, a cutting head of the lithotripter extends out of the suction opening and is configured to break calculus, and when in the second state, the cutting head of the lithotripter retracts to the suction opening and is configured to break calculus blocked in the suction opening.

According to the break-during-suction type surgical ureteroscope of the present application, the ureteroscope main body further includes a crushed calculus channel in communication with the suction channel, the lithotripter is telescopically located in the crushed calculus channel, and when the lithotripter is in the first state, the cutting head extends into the suction channel through the crushed calculus channel to extend out of the suction opening.

According to the break-during-suction type surgical ureteroscope of the present application, the crushed calculus channel includes a main body section and a communication section extending between the main body section and the suction channel, and the communication section is in communication with the suction channel and the main body section.

According to the break-during-suction type surgical ureteroscope of the present application, an angle formed between a central axis of the communication section and a central axis of the suction channel ranges from 0° to 45°.

According to the break-during-suction type surgical ureteroscope of the present application, the tube structure body has a front end surface and an outer peripheral surface, the suction opening is formed on the front end surface, and the front end surface of the tube structure body extends obliquely forward from a first side of the outer peripheral surface to a second side opposite to the first side along an axial direction of the ureteroscope main body.

According to the break-during-suction type surgical ureteroscope of the present application, when the lithotripter is in the second state, the cutting head of the lithotripter is located in a middle area of the suction opening.

According to the break-during-suction type surgical ureteroscope of the present application, when the lithotripter is in the second state, a front end of the cutting head is coplanar with the front end surface.

According to the break-during-suction type surgical ureteroscope of the present application, the crushed calculus channel is located on a lateral side of the suction channel.

According to the break-during-suction type surgical ureteroscope of the present application, the crushed calculus channel extends between the suction channel and the rear end portion of the ureteroscope main body, and the crushed calculus channel is provided with a communication opening in communication with the suction channel and the crushed calculus channel.

According to the break-during-suction type surgical ureteroscope of the present application, the operating portion includes a first operating end in communication with the perfusion channel, a second operating end in communication with the suction channel, and a third operating end in communication with the crushed calculus channel.

According to the break-during-suction type surgical ureteroscope of the present application, the perfusion opening of the perfusion channel has a first orientation, so as to allow fluid to be injected into a renal pelvis from the perfusion opening along the perfusion channel in a first direction directed by the first orientation, and the suction opening of the suction channel has a second orientation forming a predetermined angle with the first orientation, so as to allow the fluid to be sucked into the suction channel from the suction opening in a second direction directed by the second orientation after being diverted in the renal pelvis to form a fluid loop.

According to the break-during-suction type surgical ureteroscope of the present application, the tube structure body has a front end surface and an outer peripheral surface formed on the front end surface, the perfusion opening is formed on the outer peripheral surface of the tube structure body, and the suction opening is formed on the front end surface of the tube structure body.

Further objects and advantages of the present application will become more fully apparent from an understanding of the following description and drawings.

These and other objects, features, and advantages of the present application will become more fully apparent from the following detailed description, drawings, and claims.

BRIEF DESCRIPTION OF THE DRAWINGS

The above and other objects, features and advantages of the present application will become more obvious through more detailed description of the embodiments of the present application in combination with the accompanying drawings. The accompanying drawings are used to provide a further understanding of the embodiments of the present application and constitute a part of the specification. Together with the embodiments of the present application, the drawings are used to explain the present application and do not constitute a limitation of the present application. In the drawings, the same reference numbers generally represent the same components or steps.

DETAILED DESCRIPTION OF THE EMBODIMENTS

Hereinafter, example embodiments according to the present application will be described in detail with reference to the accompanying drawings. Obviously, the described embodiments are only some embodiments of the present application, not all embodiments of the present application. It should be understood that the present application is not limited to the example embodiments described herein.

Overview of the Present Application

As described above, during the process of breaking calculus through a ureteroscope, when a size of the calculus is large, it is difficult to pulverize the calculus after the calculus is crushed to a calculus with equivalent diameter of 2 mm by conventional ureteroscope, and it is also difficult to discharge the crushed calculus out of the patient's body through an effective discharging mechanism. Residual crushed calculus is one of the main causes of high recurrence rate of calculus.

In the solution, the ureteroscope includes a crushed calculus discharging mechanism to discharge the crushed calculus out of a body in time. However, during practical operation, the crushed calculus is easily blocked in the discharging mechanism of the ureteroscope and is difficult to be discharged from the patient's body.

Figure 1:
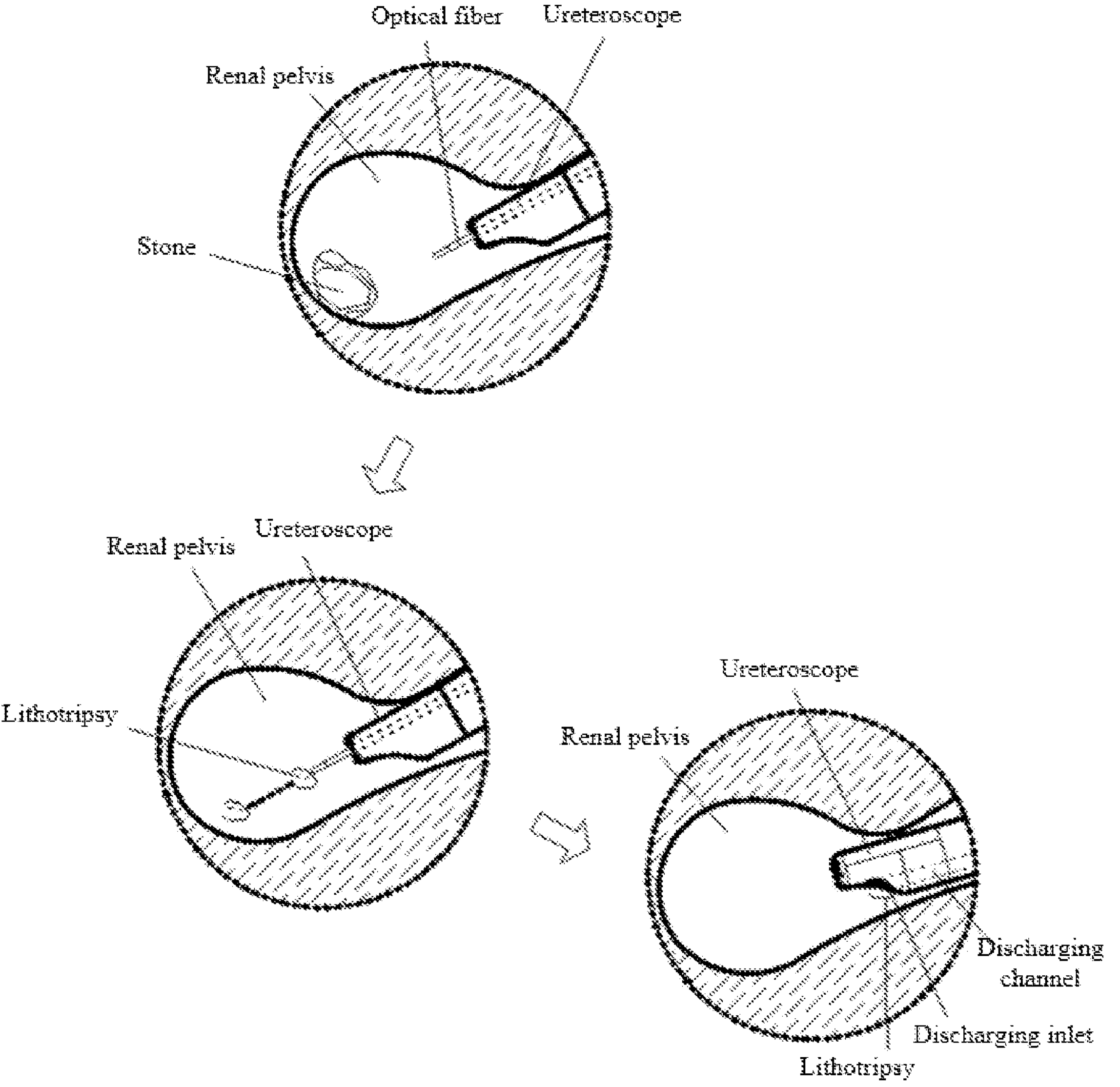
FIG. 1 is a schematic view of an operation of a ureteroscope in the prior art.

Specifically, in order to discharge a crushed calculus, some ureteroscopes use the principle of negative pressure suction to suck the crushed calculus to a discharging channel and the crushed calculus is discharged out of the body through the discharging channel. Taking the removal of calculus in the renal pelvis through the ureteroscope as an example, as shown in FIG. 1, first, an optical fiber used to crush the calculus can extend from a front end of the ureteroscope and emit laser, which can generate strong impact force. Then, the laser acts on the calculus. Since the calculus is embedded in the renal pelvis, the calculus is resisted by the kidney after being impacted and is difficult to move backward, so that the calculus bears most of the energy of the laser, and is then broken. However, the calculus that has just been broken is in a movable state. When the laser acts on the crushed calculus (i.e., lithotripsy), the crushed calculus is not fixed, and will be bounced away after being subjected to the impact force, which makes it difficult to further break the crushed calculus. Then, the crushed calculus will be sucked to a discharging inlet of the discharging channel. When the large-sized crushed calculus is sucked to the discharging inlet of the discharging channel, or when a large amount of crushed calculus rush to the discharging inlet at the same time, the discharging inlet will be blocked, resulting in that the crushed calculus is difficult to be discharged.

Inventors of the present application proposes an "break-during-suction type" calculus discharging solution, which prevents the crushed calculus from being blocked at a suction opening of a suction channel capable of discharging the crushed calculus through the cooperation between sucking and breaking the crushed calculus. Specifically, while the crushed calculus is sucked to the suction opening by the negative pressure in the suction channel, the crushed calculus is further broken by a lithotripter located at the suction opening.

In view of the above, the present application provides a break-during-suction type surgical ureteroscope, which includes: a ureteroscope main body having a front end portion and a rear end portion, the ureteroscope main body including a tube structure body; at least one perfusion channel extending from the rear end portion to the front end portion in the tube structure body, the at least one perfusion channel providing with at least one perfusion opening located at the front end portion; and a suction channel extending from the front end portion to the rear end portion in the tube structure body, the suction channel providing with a suction opening located at the front end portion; an operating portion operably coupled to the rear end portion of the ureteroscope main body; and a lithotripter movably provided in the tube structure body to switch between a first state and a second state. When in the first state, a cutting head of the lithotripter extends out of the suction opening and is configured to break calculus. When in the second state, the cutting head of the lithotripter retracts to the suction opening and is configured to break calculus blocked in the suction opening.

Exemplary Ureteroscope

Referring to FIG. 2 to FIG. 11D, the break-during-suction type surgical ureteroscope 100 according to an embodiment of the present application is illustrated. For ease of description, the break-during-suction type surgical ureteroscope 100 is described by taking an example in which the break-during-suction type surgical ureteroscope 100 is used to treat a calculus c in a renal pelvis p.

The break-during-suction type surgical ureteroscope 100 may be configured to examine the condition of a kidney, crush the calculus c in the renal pelvis p, and guide the discharge of the crushed calculus. In the embodiment of the present application, the break-during-suction type surgical ureteroscope 100 includes a ureteroscope main body 10 having a front end portion 110 and a rear end portion 120, an operating portion 20 operably coupled to the rear end portion 120 of the ureteroscope main body 10, and a lithotripter 30 configured to break the calculus.

Figure 2:
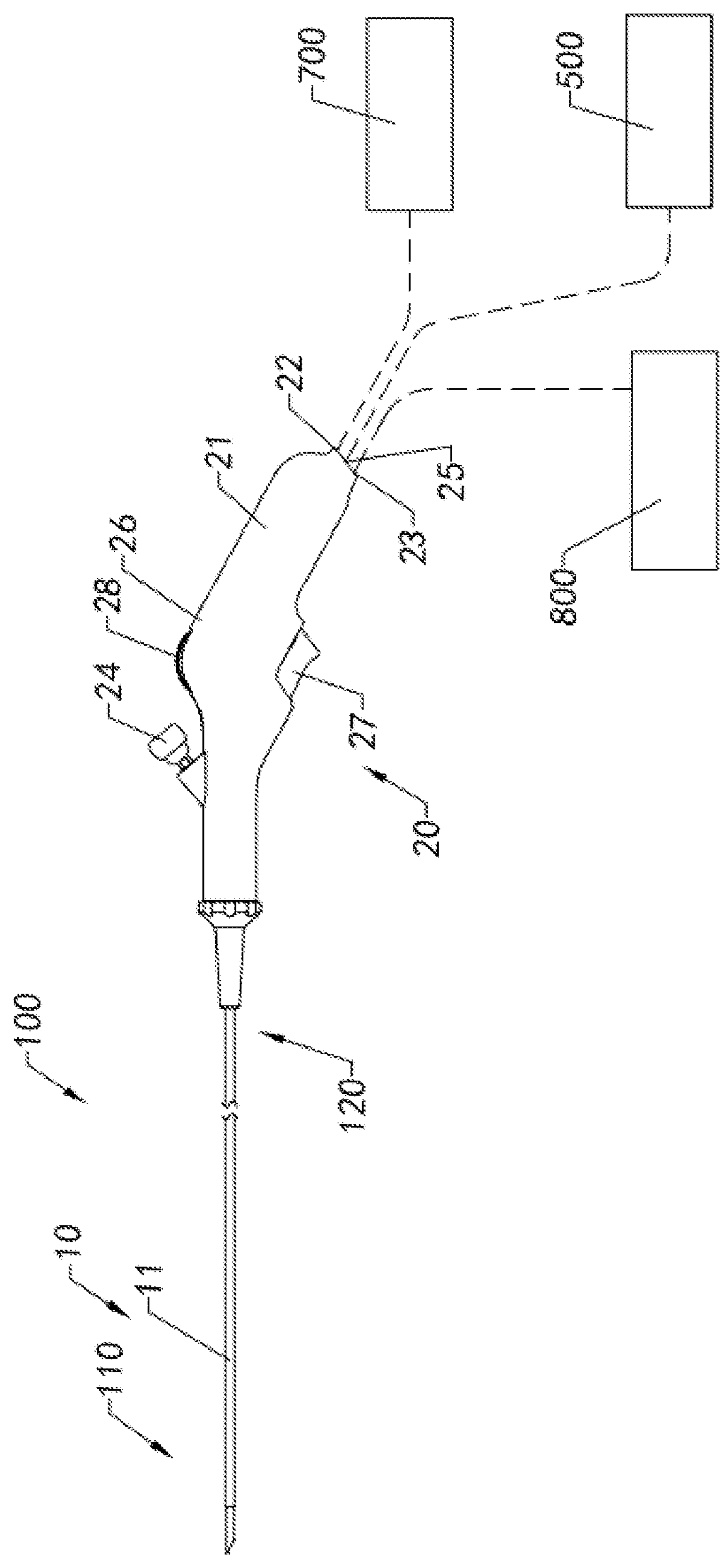
FIG. 2 is a schematic view of a break-during-suction type surgical ureteroscope according to an embodiment of the present application.
Figure 3:
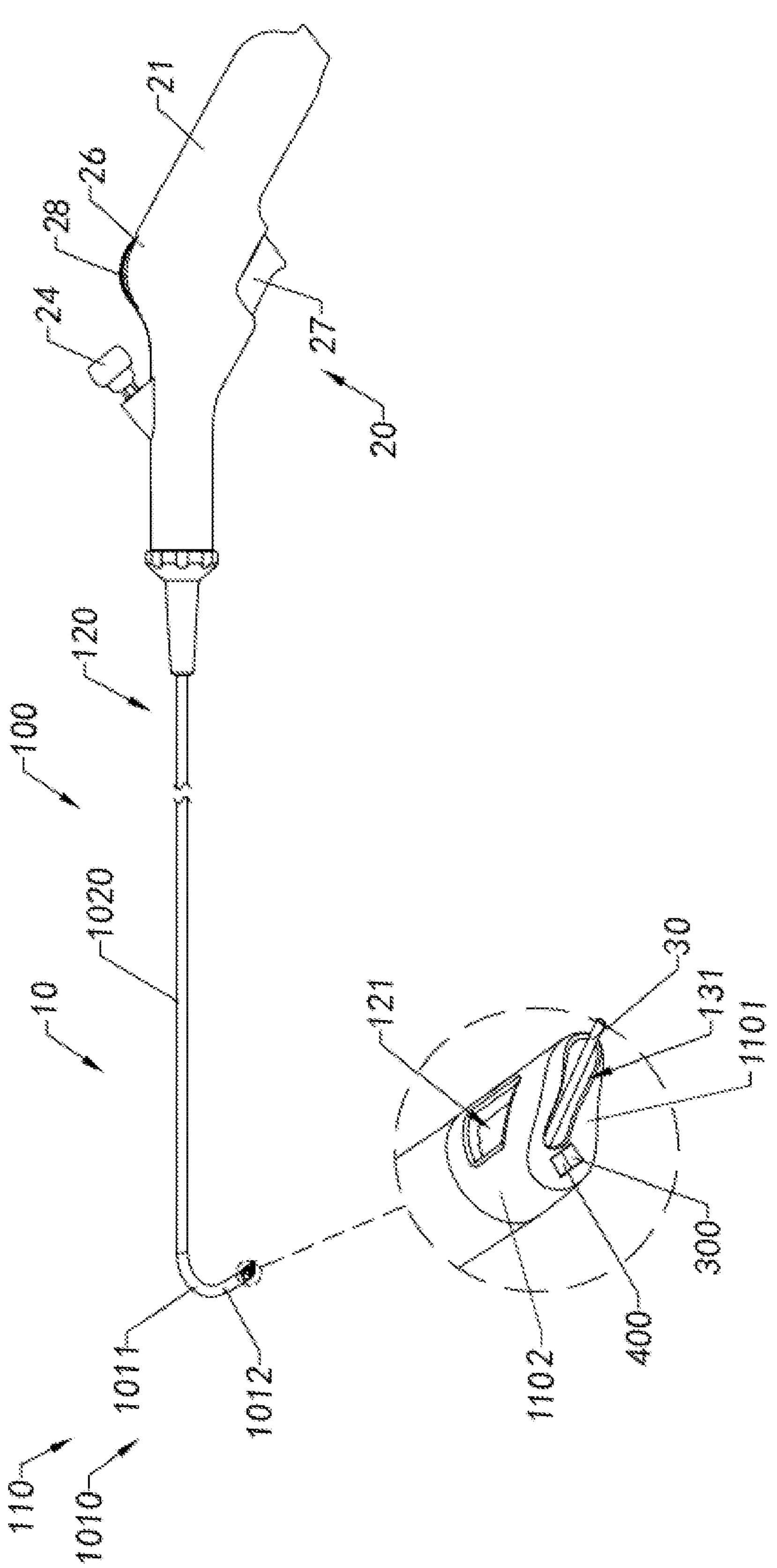
FIG. 3 is another schematic view of the break-during-suction type surgical ureteroscope according to an embodiment of the present application.

In practical operation, the ureteroscope main body 10 can be inserted into a ureter or kidney from a ureter as an insertion portion of the break-during-suction type surgical ureteroscope 100. An image acquisition device 300 and a light source 400 can be provided on the ureteroscope main body 10 to capture images of the kidney and calculus located in the kidney. Preferably, the ureteroscope main body 10 has a smooth outer surface, or the outer surface of the ureteroscope main body 10 is smooth after entering the patient's body, so that the ureteroscope main body 10 can smoothly enter the kidney. As shown in FIG. 2, as a bridge between the break-during-suction type surgical ureteroscope 100 and an external device, the operating portion 20 can be communicatively connected to an image outputting device 500 (for example, a computer communicatively connected to the image acquisition device 300) to acquire the image of the kidney, so that the user can conveniently observe the condition of the calculus c in the renal pelvis p. In addition, other functional operations can be performed by the operating portion 20 on the operable members (e.g., the lithotripter 30, a guiding mechanism 600, a fluid injection device 700, and a suction device 800). For example, the calculus c in the renal pelvis p is broken by a holmium laser entering the ureteroscope main body 10 through the operating portion 20, and for another example, the crushed calculus in the kidney is sucked by the suction device 800 in communication with the ureteroscope main body 10 through the operating portion 20.

Figure 4:
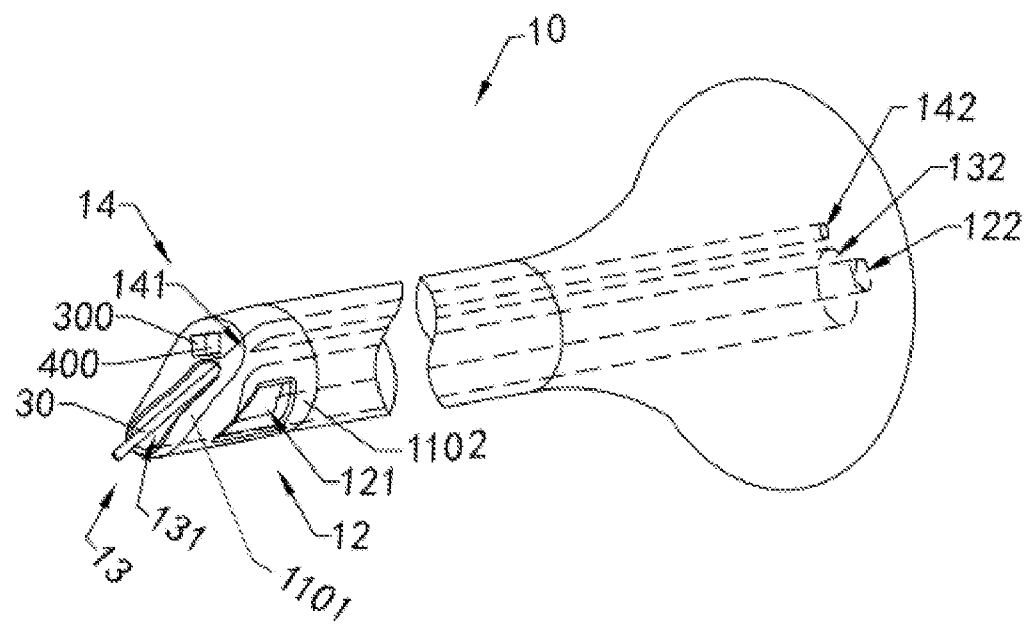
FIG. 4 is a schematic view of a ureteroscope main body of the break-during-suction type surgical ureteroscope according to an embodiment of the present application.
Figure 5A:
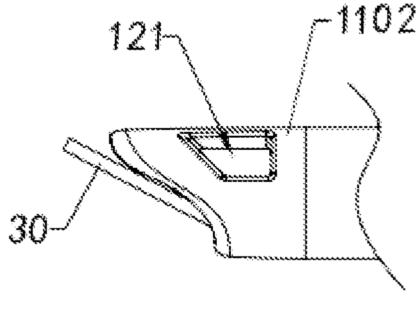
FIG. 5A is a first partial schematic view of the ureteroscope main body of the break-during-suction type surgical ureteroscope according to an embodiment of the present application.
Figure 5B:
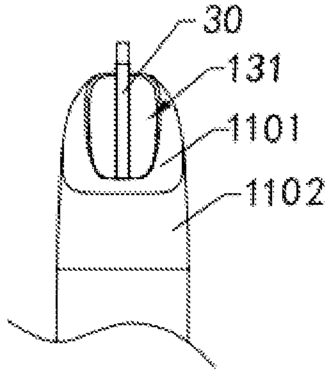
FIG. 5B is a second partial schematic view of the ureteroscope main body of the break-during-suction type surgical ureteroscope according to an embodiment of the present application.
Figure 5C:
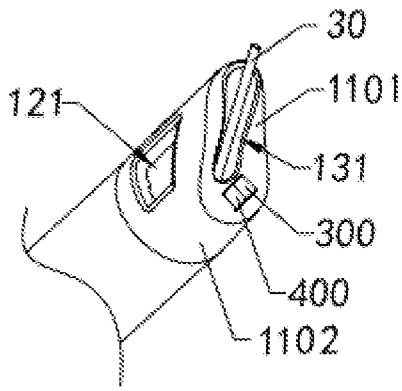
FIG. 5C is a third partial schematic view of a ureteroscope main body of the break-during-suction type surgical ureteroscope according to an embodiment of the present application.
Figure 5D:
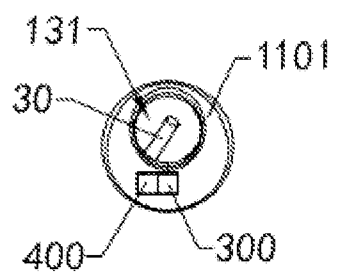
FIG. 5D is a fourth partial schematic view of the ureteroscope main body of the break-during-suction type surgical ureteroscope according to an embodiment of the present application.

Specifically, referring to FIG. 4, the ureteroscope main body 10 includes a tube structure body 11, at least one perfusion channel 12, and a suction channel 13. The at least one perfusion channel 12 extends from the rear end portion 120 to the front end portion 110 in the tube structure body 11. The suction channel 13 extends from the front end portion 110 to the rear end portion 120 in the tube structure body 11. Preferably, the perfusion channel 12 and the suction channel 13 are independent from each other, so that the fluid is guided to impact the crushed calculus in the kidney through the perfusion channel 12, and the fluid carrying the crushed calculus can be sucked to the suction channel 13 simultaneously, and mutual interference between impacting crushed calculus and sucking crushed calculus is avoided.

The at least one perfusion channel 12 has at least one perfusion opening 121 located at the front end portion 110 and at least one first operating opening 122 in communication with the at least one perfusion opening 121. The fluid can reach the kidney from the perfusion opening 121 and impact the crushed calculus in the kidney. The suction channel 13 has a suction opening 131 located at the front end portion 110 and a second operating opening 132 in communication with the suction opening 131. The crushed calculus can be sucked to the suction opening 131 and enters the suction channel 13 from the suction opening 131, so as to be discharged through the suction channel 13.

Correspondingly, the operating portion 20 includes an operating body 21, a first operating end 22 provided on the operating body 21 and in communication with the perfusion channel 12, and a second operating end 23 provided on the operating body 21 and in communication with the suction channel 13. The operating portion 20 is in communication with the perfusion channel 12 through the first operating end 22 in communication with the first operating opening 122, and is in communication with the suction channel 13 through the second operating end 23 in communication with the second operating opening 132. The first operating end 22 is configured to be connected the fluid injection device 700 and allow the fluid injection device 700 to inject fluid into the renal pelvis p through the perfusion channel 12 to impact crushed calculus. The second operating end 23 is configured to be connected to the suction device 800 (e.g., an air pump) and allow the suction device 800 to suck fluid and crushed calculus adjacent to the suction channel 13 through the suction channel 13. In order to control the negative pressure in the suction channel 13, referring to FIGS. 3 and 4, in an embodiment of the present application, the operating portion 20 further includes a negative pressure regulator 27 configured to adjust an air pressure in the suction channel 13.

It should be understood that the functions of the first operating end 22 and the second operating end 23 are not limited herein. The first operating end 22 and the second operating end 23 are further configured to allow other devices to perform other functional operations. For example, the first operating end 22 is configured to allow the guiding mechanism 600 to extend through the perfusion channel 12 and guide the ureteroscope main body 10 to a target position. It should also be understood that the operating portion 20 may also include other operating ends to allow other devices to perform other functional operations.

Specifically, in the embodiment of the present application, the suction channel 13 not only allows the crushed calculus to be sucked to the suction opening 131, but also allows a cutting head 32 of the lithotripter 30 to extend out of the suction opening 131 or retract to the suction opening 131 to break the crushed calculus blocked in the suction opening 131. Specifically, the lithotripter 30 includes a calculus breaking body 31 and the cutting head 32 formed on the calculus breaking body 31. The lithotripter 30 is movably provided in the tube structure body 11 to switch between the first state and the second state. When the lithotripter 30 is in the first state, the cutting head 32 of the lithotripter 30 extends out of the suction portion 131 to break the crushed calculus. When the lithotripter 30 is in the second state, the cutting head 32 of the lithotripter 30 is retracted to the suction portion 131 to break the crushed calculus blocked in the suction portion 131. That is, the lithotripter 30 can be used not only to break the calculus c formed in the renal pelvis p, but also to further break the calculus that are broken and blocked in the channel configured to discharge the calculus.

It should be noted that when the lithotripter 30 is in the first state, the lithotripter 30 extends from the suction opening 131, the crushed calculus is opposite to the suction opening 131, and is more easily sucked to the suction opening 131, which can improve the calculus discharging efficiency.

In practical operation, some of the crushed calculi are large in size, and will block the suction opening 131 when reaching the suction opening 131, so that it is difficult to be discharged and other calculus are prevented from being discharged, which affects the calculus discharging efficiency, and therefore the crushed calculus needs to be further broken. However, the calculus that has just been broken is in a movable state, when the lithotripter 30 is used to break the movable crushed calculus, on the one hand, the lithotripter 30 is difficult to aim due to the continuous change of the position of the movable crushed calculus, on the other hand, as described above, the crushed calculus is not fixed and will be bounced away after being subjected to the impact force, which makes it difficult to remove the crushed calculus. In the embodiment of the present application, sucking crushed calculus and breaking crushed calculus can cooperate with each other, so as to achieve accurate breaking of the crushed calculus and improve the calculus discharging efficiency. Specifically, the crushed calculus can be sucked to the suction opening 131, and the lithotripter 30 can be switched to the second state, that is, the lithotripter 30 retracts to the suction opening 131, and then precisely breaks the crushed calculus located at the suction opening 131, and the crushed calculus can enter the suction channel 13 through the suction opening 131, and then be removed out of the body. In addition, the crushed calculus blocked in the suction opening 131 is stuck at the suction opening 131, and the position is relatively stable. During the process of breaking the crushed calculus by the lithotripter 30, the crushed calculus abuts against an inner peripheral wall of the suction channel 13. When the impact force generated by the lithotripter 30 acts on the crushed calculus, the crushed calculus will receive most of the energy generated by the lithotripter 30, so that it is easier to be crushed. In this way, the crushed calculus can be led out relatively quickly, so as to improve the calculus discharging efficiency.

When too much lithotripsies are sucked to the suction opening 131 at the same time, the suction opening 131 may also be blocked. The lithotripter 30 can also be switched to the second state, at least a part of the crushed calculus is broken or a plurality of crushed calculus are scattered, so that the suction opening 131 remains open, so as to allow the crushed calculus to quickly enter the suction channel 13 through the suction opening 131 and then be removed out of the body, thereby improving the calculus discharging efficiency.

It should be noted that the type of the lithotripter 30 is not limited herein, and the lithotripter 30 may be a holmium laser or other type of tool capable of breaking the calculus c. The holmium laser can emit a laser, and the energy generated by the holmium laser can enable the water between the calculus c and the holmium laser to form tiny vacuoles, and the energy is transferred to the calculus c to break the calculus c. During the process of breaking the calculus c by the holmium laser, the water absorbs a large amount of energy, which can reduce the damage to the tissue around the calculus c by the holmium laser.

Further, the ureteroscope main body 10 further includes a crushed calculus channel 14 in communication with the suction channel 13, and the lithotripter 30 is telescopically located in the crushed calculus channel 14. When the lithotripter 30 is in the first state, the cutting head 32 extends through the crushed calculus channel 14 and extends to the suction channel 13 to extend out of the suction opening 131. That is, the cutting head 32 of the lithotripter 30 can enter the suction channel 13 along the crushed calculus channel 14 and extend out of the suction opening 131.

In the embodiment of the present application, the crushed calculus channel 14 extends between the suction channel 13 and the rear end portion 120 of the ureteroscope main body 10, and the crushed calculus channel 14 is provided with a communication opening 141 in communication with the suction channel 13 and a third operating opening 142 in communication with the communication opening 141 and located at the rear end portion 120.

Correspondingly, the operating portion 20 further includes a third operating end 24 in communication with the crushed calculus channel 14, and the operating portion 20 is in communication with the crushed calculus channel 14 through the third operating end 24 in communication with the third operating opening 142. The third operating end 24 allows the lithotripter 30 to extend through and enter the crushed calculus channel 14 and the suction channel 13 in communication with the crushed calculus channel 14 from the third operating opening 142 in communication therewith. That is, the lithotripter 30 can enter the crushed calculus channel 14 and the suction channel 13 in communicating with the crushed calculus channel 14 from the third operating opening 142 through the third operating end 24 of the operating portion 20, and then enter the kidney to break the calculus c.

In the embodiment of the present application, the crushed calculus channel 14 includes a main body section 143 and a communication section 144 extending between the main body section 143 and the suction channel 13. The communication section 144 is provided with the communication opening 141 in communication with the suction channel 13 and is in communication with the suction channel 13 through the communication opening 141, and the communication section 144 extends obliquely upward from the main body section 143 to the suction channel 13 along a predetermined direction. In an embodiment of the present application, an angle between the predetermined direction and a central axis of the suction channel 13 is 0° to 45°. Correspondingly, an angle between a central axis of the communication section 144 and the central axis of the suction channel 13 is 0° to 45°. The cutting head 23 of the lithotripter 30 can extend into the suction opening 131 along the communication section 144 at an angle of 45° with respect to the central axis of the suction channel 13. It should be understood that the steeper the communication section 144 is, the closer the central axis of the communication section 144 is to coincide with the central axis of the suction channel 13, and the quicker the lithotripter 30 extends through the suction channel 13 and extends out of the suction opening 131. The angle between the communication section 144 and the central axis of the suction channel 13 may be other angles, for example, 30° and 60°, which is not limited herein.

Further, in this embodiment, when the lithotripter 30 is in the second state, the cutting head 32 of the lithotripter 30 is located in a middle area of the suction opening 131. Specifically, during the process of switching the lithotripter 30 from the first state to the second state, the lithotripter 30 can retract along the communication section 144 in a direction opposite to the predetermined direction. When the lithotripter 30 retracts to the suction opening 131, the cutting head 32 of the lithotripter 30 is located in the middle area of the suction opening 131.

It should be noted that the position where the crushed calculus blocked at the suction opening 131 abuts against the inner peripheral wall of the suction channel is uncertain. When the crushed calculus is broken from a peripheral area of the suction opening 131 formed around the middle area, the crushed calculus may still be stuck at the suction opening 131, and the calculus breaking efficiency is relatively low. For example, a first position and a second position of the crushed calculus abut against an inner peripheral wall forming a first peripheral area and an inner peripheral wall forming a second peripheral area, respectively, and are further stuck at the suction opening 131. When the lithotripter 30 breaks the first position of the crushed calculus from the first peripheral area or the second position of the crushed calculus from the second peripheral area, as the crushed calculus is broken at the first position or the second position, the crushed calculus may break away from the suction opening 131 and enter the suction channel 13. However, when the lithotripter 30 breaks a position of the crushed calculus hanging in the suction opening 131, the first position or the second position of the crushed calculus may still abut against the inner peripheral wall and be stuck in the suction opening 131. When the lithotripter 30 breaks the crushed calculus from the middle area of the suction opening 131, a middle position of the crushed calculus corresponding to the middle area of the suction opening 131 is crushed, and the crushed calculus will break away from the suction opening 131. Therefore, preferably, when the lithotripter 30 is in the second state, the cutting head 32 of the lithotripter 30 is located in the middle area of the suction opening 131. It should be understood that when the lithotripter 30 is in the second state, the cutting head 32 of the lithotripter 30 may also be located at other positions of the suction opening 131, which is not limited herein.

In this embodiment, the tube structure body 11 has a front end surface 1101 and an outer peripheral surface 1102 formed on an outer peripheral side of the front end surface 1101. The front end surface 1101 of the tube structure body 11 extends obliquely forward from a first side of the outer peripheral surface 1102 to a second side opposite to the first side along an axial direction of the ureteroscope main body 10. For example, referring to FIG. SA, the front end surface 1101 of the tube structure body 11 extends obliquely forward from a lower side of the outer peripheral surface 1102 to an upper side opposite to the lower side along the axial direction defined by the ureteroscope main body 10.

Specifically, the front end surface 1101 may be designed as a convex slope, a concave slope, a wave slope, or other types of slopes formed between the first side and the second side of the outer peripheral surface 1102, which is not limited herein. In an embodiment of the present application, the front end surface 1101 is designed as a concave wavy slope formed in a middle portion between the first side and the second side of the outer peripheral surface 1102.

It should be understood that, in other embodiments, the front end surface 1101 of the tube structure body 11 may also be designed such that the front end surface 1101 of the tube structure body 11 extends in parallel from the first side of the outer peripheral surface 1102 to the second side opposite to the first side along the axial direction of the ureteroscope main body 10 (i.e., an end of the front end surface 1101 adjacent to the first side of the suction channel 13 is coplanar with an end of the front end surface 1101 adjacent to the second side of the suction channel 13 in the axial direction of the ureteroscope main body 10), which is not limited herein.

Further, the suction opening 131 is formed on the front end surface 1101, and the suction opening 131 extends obliquely forward from the first side of the suction channel 13 to the second side opposite to the first side along the axial direction of the ureteroscope main body 10. The first side of the outer peripheral surface 1102 corresponds to a first side of the suction channel 13, and the second side of the outer peripheral surface 1102 corresponds to the second side of the suction channel 13. Correspondingly, a shape of the suction opening 131 is substantially elliptical. When the lithotripter 30 is in the second state, a front end of the cutting head 32 of the lithotripter 30 is coplanar with a surface formed by an outer edge of the suction opening 131. The outer edge of the suction opening 131 refers to an inner peripheral edge of the inner peripheral wall of the suction channel 13. Correspondingly, when the suction opening 131 is formed on the front end surface 1101, the front end of the cutting head 32 is coplanar with the front end surface 1101.

It should be noted that when the front end surface 1101 is designed to extend obliquely forward from the first side to the second side of the outer peripheral surface 1102 along the axial direction of the ureteroscope main body 10, a relatively large distribution space can be provided for the suction opening 131. Correspondingly, a size of the suction opening 131 is relatively increased, which can allow more calculus to pass through the suction channel 13, thereby preventing the calculus from blocking the suction opening 131 and improving the calculus discharging efficiency.

Figure 6A:
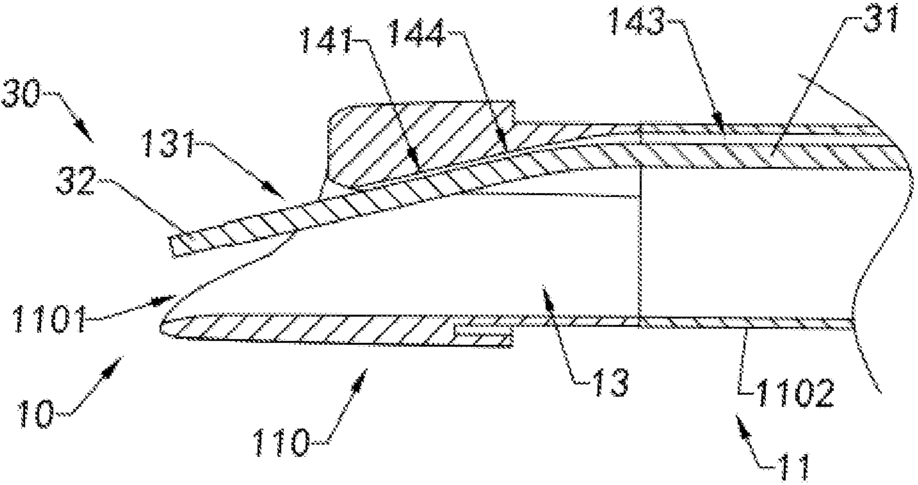
FIG. 6A is a partial cross-sectional view of the ureteroscope main body of a break-during-suction type surgical ureteroscope according to an embodiment of the present application.
Figures 6B, 7A:
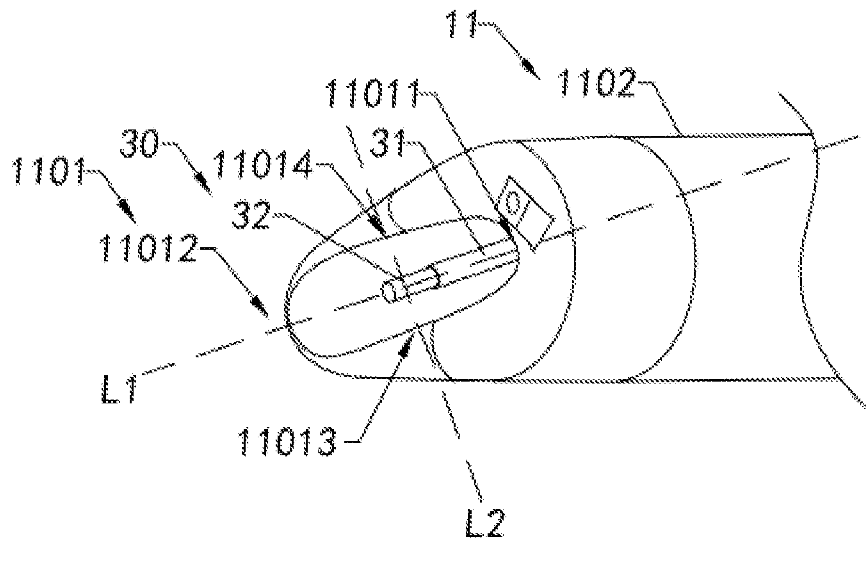
FIG. 6B is a partial perspective view of the ureteroscope main body of the break-during-suction type surgical ureteroscope according to an embodiment of the present application.
FIG. 7A is a partial cross-sectional view of the ureteroscope main body of the break-during-suction type surgical ureteroscope according to an alternative embodiment of the present application.
Figure 7B:
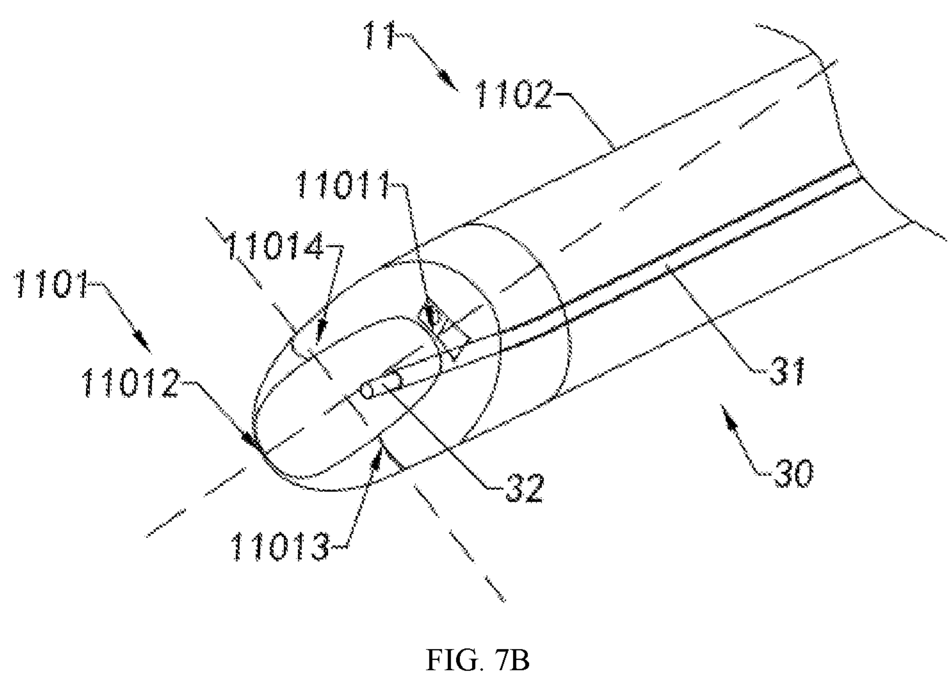
FIG. 7B is a partial perspective view of the ureteroscope main body of the break-during-suction type surgical ureteroscope according to a variation of an alternative embodiment of the present application.
Figure 8A:
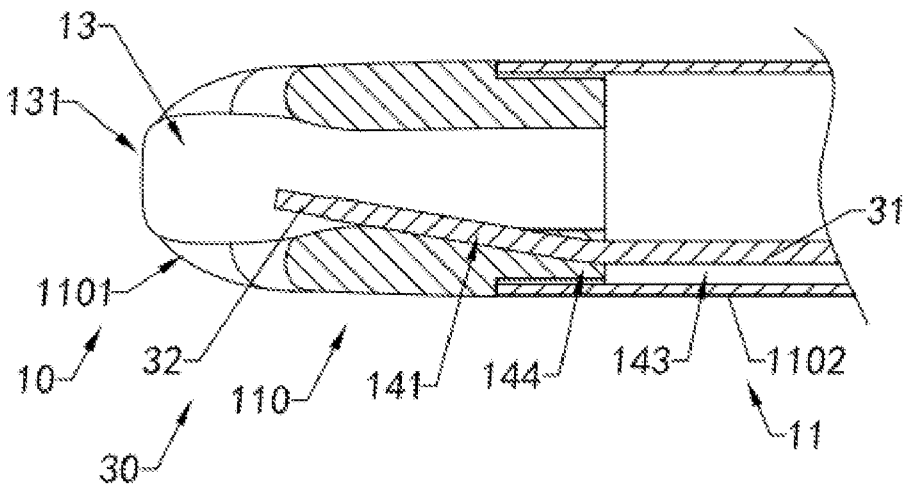
FIG. 8A is a partial cross-sectional view of the ureteroscope main body of the break-during-suction type surgical ureteroscope according to another alternative embodiment of the present application.
Figure 8B:
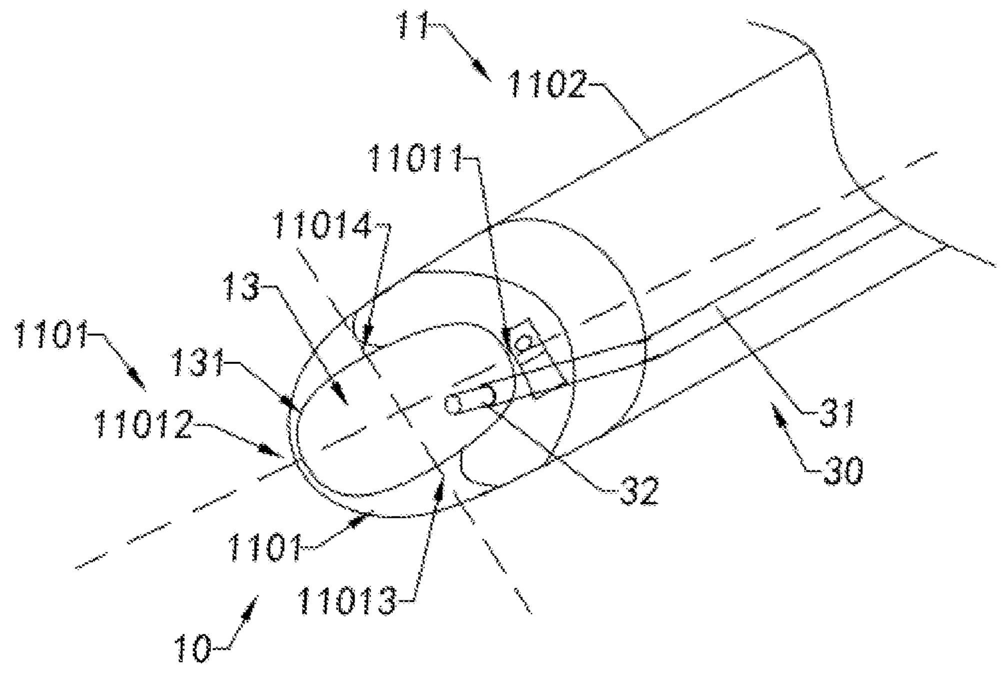
FIG. 8B is a partial perspective view of the ureteroscope main body of the break-during-suction type surgical ureteroscope according to another alternative embodiment of the present application.
Figure 9A:
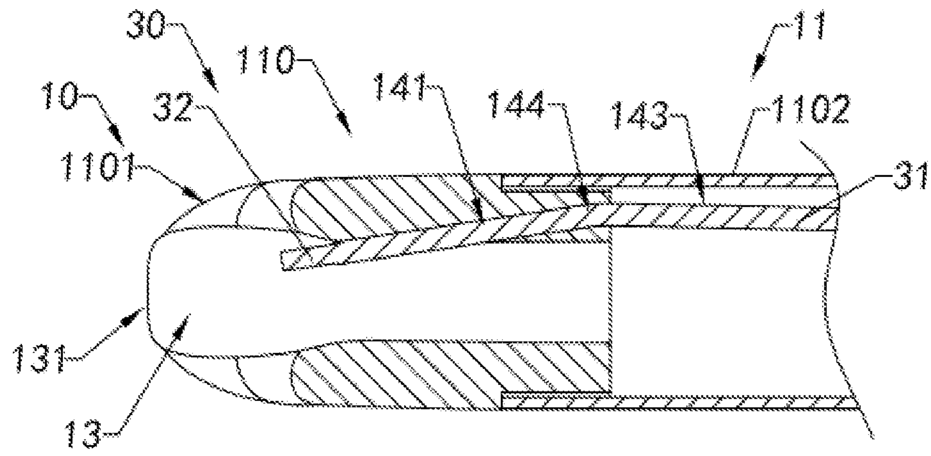
FIG. 9A is a partial cross-sectional view of the ureteroscope main body of the break-during-suction type surgical ureteroscope according to yet another alternative embodiment of the present application.
Figure 9B:
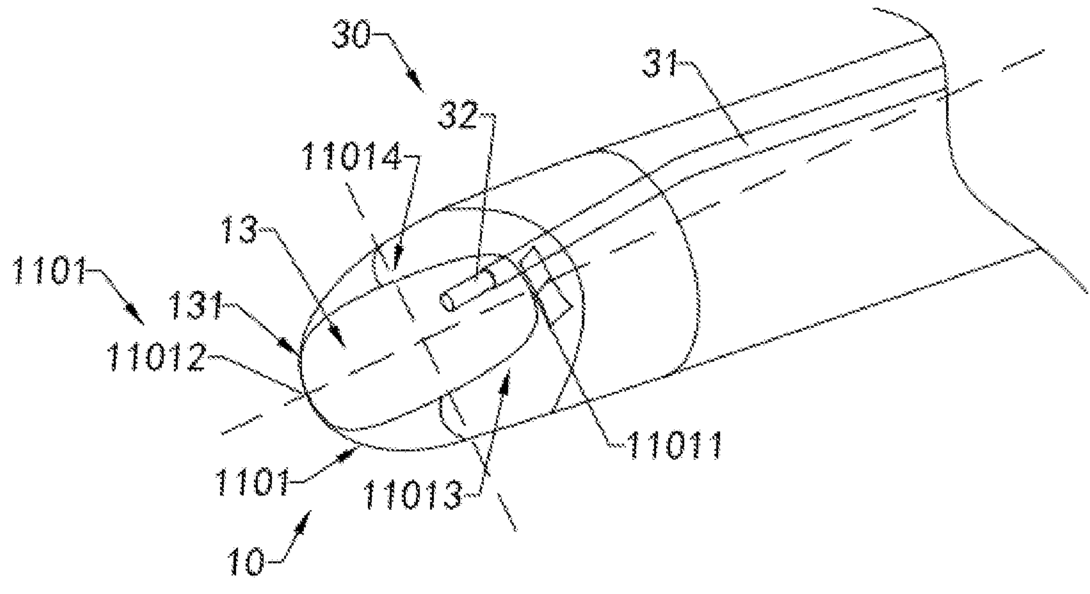
FIG. 9B is a partial perspective view of the ureteroscope main body of the break-during-suction type surgical ureteroscope according to yet another alternative embodiment of the present application.

In the embodiment of the present application, the crushed calculus channel 14 is formed on a lateral side of the suction channel 13. For example, the crushed calculus channel 14 may be formed on the first side of the suction channel 13, as shown in FIGS. 6A and 6B. The crushed calculus channel 14 may also be formed on the second side of the suction channel 13 opposite to the first side, as shown in FIGS. 7A and 7B. The crushed calculus channel 14 may also be formed on a third side between the first side and the second side of the suction channel 13, as shown in FIGS. 8A and 8B. Alternatively, the crushed calculus channel 14 may be formed on a fourth side of the suction channel 13 opposite to the third side, as shown in FIGS. 9A and 9B.

When the front end surface 1101 and the suction opening 131 are designed such that the front end surface 1101 extends obliquely forward from the first side of the outer peripheral surface 1102 to a second side opposite to the first side along the axial direction of the ureteroscope main body 10, and the suction opening 131 extends obliquely forward from the first side of the suction channel 13 to the second side opposite to the first side along the axial direction of the ureteroscope main body 10, the overall shape of the suction opening 131 is similar to an ellipse. The suction opening 131 has a long axis L1 and a short axis L2, the suction opening 131 has a first end point 11011 and a second end point 11012 on the long axis L1, and a third end point 11013 and a fourth end point 11014 on the short axis L2. The first end point 11011 is opposite to the second end point 11012, and the first end point 11011 of the front end surface 1101 is rearward relative to the second end point 11012, that is, the first end point 11011 is located behind the second end point 11012. The third end point 11013 is opposite to the fourth end point 11014, and both are located between the first end point 11011 and the second end point 11012.

The first side refers to a side adjacent to the first end point 11011, the second side refers to a side adjacent to the second end point 11012, the third side refers to a side adjacent to the third end point 11013, and the fourth side refers to a side adjacent to the fourth end point 11014. It should be understood that the crushed calculus channel 14 may be formed on other sides of the suction channel 13, for example, a fifth side between the first side and the third side, which is not limited herein.

It should be noted that the crushed calculus channel 14 is formed on the side of the suction channel 13, and the lithotripter 30 is telescopically arranged in the crushed calculus channel 14. When the lithotripter 30 is in the first state or the second state, only a front portion the lithotripter 30 including the cutting head 32 is located in the suction channel 13, and a rear portion of the lithotripter 30 is located in the crushed calculus channel 14 without occupying the space in the suction channel 13. In this way, the lithotripter 30 can be prevented from affecting the crushed calculus passing through the suction channel 13.

In an alternative embodiment of the present application, the crushed calculus channel 14 may be formed in the suction channel 13 or other channels of the tube structure body 11, which is not limited herein.

In the embodiment of the present application, the formation mode of the perfusion channel 12, the suction channel 13, and the crushed calculus channel 14 is not limited herein. The perfusion channel 12, the suction channel 13, and the crushed calculus channel 14 may be formed by a plurality of holes of the tube structure body 11, or may be formed by a plurality of hollow tubes, which is not limited herein.

In practical operation, after the ureteroscope main body 10 is inserted into the kidney, the lithotripter 30 (e.g., a holmium laser) may extends through the ureteroscope main body 10 to reach the kidney and break the calculus c. During the process of breaking the calculus c by the holmium laser, the perfusion channel 12 can guide the fluid to be injected from the perfusion opening 121 to impact the crushed calculus and move with the crushed calculus. The air pressure in the suction channel 13 is in a negative pressure state. Therefore, when the fluid carrying the crushed calculus moves to a position adjacent to the suction opening 131, the fluid and the crushed calculus are sucked into the suction channel 13, and the fluid may be interfered by the suction force in the suction channel 13 during the process of impacting the crushed calculus.

Figure 10:
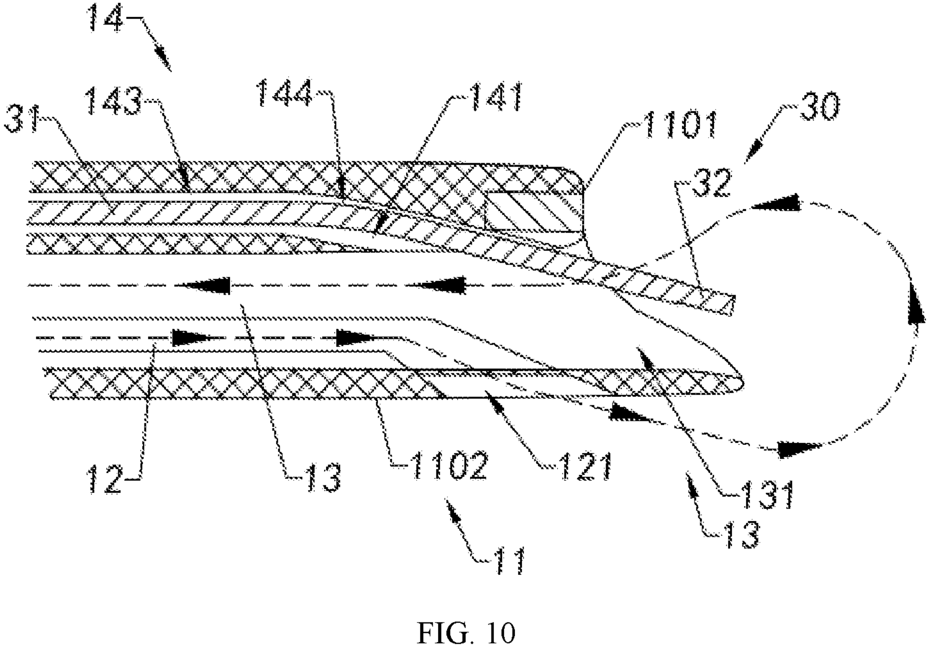
FIG. 10 is yet another partial cross-sectional view of the ureteroscope main body of the break-during-suction type surgical ureteroscope according to an embodiment of the present application.

Specifically, in some embodiments of the present application, by adjusting a relative position relationship between the perfusion opening 121 and the suction opening 131 is adjusted, and controlling a flow direction of the fluid, the suction interference on the fluid can be reduced, and the calculus discharging efficiency is improved. The perfusion opening 121 of the perfusion channel 12 has a first orientation, so as to allow fluid to be injected into the renal pelvis p from the perfusion opening 121 along the perfusion channel 12 in a first direction directed by the first orientation. The suction opening 131 of the suction channel 13 has a second orientation forming a predetermined angle with the first orientation, so as to allow the fluid to be sucked into the suction channel 13 from the suction opening 131 in a second direction directed by the second orientation after being diverted in the renal pelvis p to form a fluid loop, as shown in FIG. 10.

The second orientation is different from the first orientation, the first direction is the same as the first orientation, and the second direction is opposite to the second orientation, so that an angle between the first direction and the second direction is not 0° or 180°. That is, the first direction and the second direction are different from each other, and are not opposite to each other. In this way, the fluid injected from the perfusion opening 121 in the first direction flows back along the second direction at an angle to the first direction after being diverted to form a vortex fluid loop, which can prevent the fluid from flowing back to the suction opening 131 having the same direction as the perfusion opening 121 from in a direction opposite to the first direction after being injected from the perfusion opening 121 in the first direction, thereby reducing the interference of the negative pressure in the suction channel 13 on the fluid.

It should be noted that, in other embodiments of the present application, the first orientation and the second orientation may be the same, and the first direction and the second direction may be the same or opposite to each other, which is not limited herein.

In this embodiment of the present application, the angle between the first direction and the second direction is greater than or equal to 90° and less than 180°. In an embodiment, the second direction is parallel to or substantially the axial direction of the ureteroscope main body 10, the angle between the first direction and the axial or radial direction of the ureteroscope main body 10 is greater than 0° and less than or equal to 90°, and correspondingly, the angle between the first direction and the second direction is greater than or equal to 90° and less than 180°. In another embodiment, the first direction is parallel to or substantially the axial direction of the ureteroscope main body 10, the angle between the second direction and the axial direction is greater than 0° and less than or equal to 90°, and correspondingly, the angle between the first direction and the second direction is greater than or equal to 90° and less than 180°.

In an embodiment of the present application, the angle between a central axis of the perfusion opening 121 and a central axis of the suction opening 131 is greater than 0° and less than or equal to 90°, so that the first direction and the second direction form a preset angle.

In the embodiment of the present application, the perfusion opening 121 and the suction opening 131 are not coplanar with each other in the axial direction of the ureteroscope main body 10. In this way, a distance between the perfusion opening 121 and the suction opening 131 can be extended, as well as a movement path of the fluid, which not only can reduce the suction interference of the negative pressure in the suction channel 13 on the fluid, but also, since the fluid flows through a wider area, the fluid can carry relatively more calculus on the movement path of the fluid, which can improve the calculus discharging efficiency.

As used herein, the perfusion opening 121 and the suction opening 131 are not coplanar in the axial direction of the ureteroscope main body 10, which means that there is a height difference between the perfusion opening 121 and the suction opening 131 in the axial direction, and a distance between the perfusion opening 121 and a front end point of the ureteroscope main body 10 is different from a distance between the suction opening 131 and the front end point of the ureteroscope main body 10. In an embodiment, the distance between the perfusion opening 121 and the front end point of the ureteroscope main body 10 is greater than the distance between the suction opening 131 and the front end point of the ureteroscope main body 10, that is, the suction opening 131 is located in front of the perfusion opening 121 in the axial direction of the ureteroscope main body 10, and the suction opening 131 is closer to the front end point of the ureteroscope main body 10 than the perfusion opening 121. In another embodiment, the distance between the perfusion opening 121 and the front end point of the ureteroscope main body 10 is less than the distance between the suction opening 131 and the front end point of the ureteroscope main body 10, that is, the perfusion opening 121 is located in front of the suction opening 131, and the perfusion opening 121 is closer to the front end point of the ureteroscope main body 10 than the suction opening 131.

In a modification embodiment of the present application, the perfusion opening 121 and the suction opening 131 may be coplanar with each other in the axial direction of the ureteroscope main body 10, which is not limited herein.

In the embodiment of the present application, the perfusion opening 121 and the suction opening 131 are two openings isolated from each other. In some embodiments of the present application, the perfusion opening 121 and the suction opening 131 are respectively located on two different surfaces.

In an embodiment of the present application, referring to FIGS. 5A to 5D, the perfusion opening 121 is formed on the outer peripheral surface 1102 of the tube structure body 11, and the suction opening 131 is formed on the front end surface 1101 of the tube structure body 11. In this way, the perfusion opening 121 is opened to a lateral direction, and the suction opening 131 is opened to a forward direction. The fluid is injected into the renal pelvis p in the first direction from the perfusion opening 121 formed on the outer peripheral surface 1102 of the tube structure body 11, and after being turned around the outer peripheral surface 1102, the fluid needs to be sucked into the suction channel 13 from the suction opening 131 in the second direction, so as to form a vortex fluid loop, which can reduce the suction interference on the fluid.

Specifically, in this embodiment, the perfusion opening 121 formed on the outer peripheral surface 1102 of the tube structure body 11 mainly occupies an axial dimension of the tube structure body 11, and the suction opening 131 formed on the front end surface 1101 of the tube structure body 11 mainly occupies a radial dimension of the tube structure body 11. In this way, there is no need to adjust a ratio of space occupied by the perfusion opening 121 and the suction opening 131 in the radial direction of the tube structure body 11 under the condition that a radial size of the tube structure body 11 is limited, the sizes of the perfusion opening 121 and the suction opening 131 can be relatively increased, and the design flexibility of the shape and the number of the suction opening 131 and the perfusion opening 121 is also relatively improved. Through the reasonable arrangement of the perfusion opening 121 and the suction opening 131, the sizes of the suction opening 131 of the suction channel 13 are ensured to allow the fluid and the crushed calculus to pass through smoothly, and the liquid output volume of the perfusion opening 121 of the perfusion channel can be ensured.

When the liquid output volume of the perfusion opening 121 is relatively large, on the one hand, a range of the fluid injected from the perfusion opening 121 is relatively extended, the impact force to the crushed calculus is relatively increased, the suction interference is relatively weakened, and the calculus discharging efficiency is relatively improved. On the other hand, the ureteroscope can achieve a high liquid output volume at a relatively low liquid injection pressure, thereby reducing the risk of increased pressure in the kidney.

It should be noted that, as described above, in some embodiments of the present application, the front end surface 1101 of the tube structure body 11 is designed to extend obliquely forward from the first side of the outer peripheral surface 1102 to a second side opposite to the first side along the axial direction of the ureteroscope main body 10. It should be noted that when the front end surface 1101 is designed to extend obliquely forward from the first side to the second side of the outer peripheral surface 1102 along the axial direction of the ureteroscope main body 10, compared with the front end surface 1101 designed to extend in parallel from the first side to the second side of the suction channel 13 along the axial direction of the ureteroscope main body 10, the path of the fluid is extended, not only the suction interference is relatively weakened, but also, since the fluid flows through a wider area, the fluid can carry relatively more calculus on the movement path of the fluid, which can improve the calculus discharging efficiency.

It should be noted that a diameter size of the perfusion channel 12 is preferably equal to or slightly greater than a diameter size of the suction channel 13, so as to achieve flow balance. Herein, the diameter size of the perfusion channel 12 is equal to or slightly greater than the diameter size of the suction channel 13, which means that a sum of equivalent diameters of all the perfusion channels 12 is equal to or slightly greater than a sum of the equivalent diameters of all the suction channels 13.

In an embodiment of the present application, one suction openings 131 is provided, and two perfusion openings 121 are provided. Correspondingly, the at least one perfusion channel 12 includes a first perfusion channel and a second perfusion channel, the first perfusion channel has a first perfusion opening located at the front end portion 110, and the second perfusion channel has a second perfusion opening located at the front end portion 110. Preferably, the first perfusion opening is opposite to the second perfusion opening.

In this embodiment, an average value of a first inner diameter of the first perfusion channel and a second inner diameter of the second perfusion channel is greater than or equal to half of a diameter of the suction channel 13, a size of the perfusion opening 121 matches a size of the first perfusion channel, and a size of the suction opening 131 matches a size of the suction channel 13. Herein, an average diameter of the first perfusion channel and the second perfusion channel refer to an average value of an equivalent diameter of the first perfusion channel and an equivalent diameter of the second perfusion channel. The diameter of the suction channel 13 refers to an equivalent diameter of the suction channel 13. Specifically, an outer diameter of the tube structure body 11 is equal to 4.3 mm, the diameter of the suction channel 13 is equal to 2.2 mm, and the equivalent diameter of the first perfusion channel or the second perfusion channel is greater than or equal to 1.2 mm.

In another embodiment of the present application, the perfusion channel 12 is circumferentially formed around the suction channel 13, that is, the perfusion channel 12 is an annular channel formed around the suction channel 13, or in other words, the cross-section of the perfusion channel 12 is annular. The perfusion channel 12 has two perfusion openings 121 formed at the front end portion 110. In this embodiment, the outer diameter of the tube structure body 11 is equal to 4.3 mm, the diameter of the suction channel 13 is equal to 2.2 mm, and the equivalent diameter of the first perfusion channel or the second perfusion channel is greater than or equal to 1.2 mm.

It should be understood that the size, shape, and number of the suction opening 131 and the perfusion opening 121 are not limited herein, and the size, shape, and number of the suction opening 131 and the perfusion opening 121 can be adjusted according to actual application conditions to achieve controllable and orderly fluid circulation.

It should be noted that the positions of the suction opening 131 and the perfusion opening 121 are not limited herein. In other embodiments, the suction opening 131 and the perfusion opening 121 may be provided at other positions. In another embodiment of the present application, the suction opening 131 and the perfusion opening 121 are provided on the outer peripheral surface 1102 and the front end surface, respectively.

In yet another embodiment of the present application, both the suction opening 131 and the perfusion opening 121 are provided on the front end surface 1101 of the tube structure body 11. Specifically, in this embodiment, the at least one perfusion channel 12 includes a first perfusion channel and a second perfusion channel, the first perfusion channel has a first perfusion opening located at the front end portion 110, the second perfusion channel has a second perfusion opening located at the front end portion 110, and the first perfusion opening and the second perfusion opening are located on both sides of the suction opening 131.

In the embodiment of the present application, the break-during-suction type surgical ureteroscope 100 further includes the image acquisition device 300 and the light source 400 mounted on the tube scope main body 10, which are configured to capture images of the kidney and calculus located in the kidney. The positions of the image acquisition device 300 and the light source 400 are not limited therein. Preferably, the suction opening 131 of the suction channel 13 is located in a visible area of the image acquisition device 300, so as to acquire the situation adjacent to the suction opening 131, so that the user can conveniently observe the discharge of the crushed calculus. The light source 400 may be provided adjacent to the image acquisition device 300 to provide a sufficient amount of light for the image acquisition device 300.

Correspondingly, the operating portion 20 further includes a fourth operating end 25 communicatively connected to the image acquisition device 300. In addition, the image outputting device 500 (for example, a computer communicatively connected to the image acquisition device 300) may communicatively connected to the image acquisition device 300 through the operating portion 20 to acquire the image of the kidney, so that the user can conveniently observe the condition of the calculus c in the renal pelvis p.

It should be noted that, in order to ensure the stiffness of the ureteroscope main body 10 while ensuring that the ureteroscope main body 10 can be bent to reach different target positions, the ureteroscope main body 10 includes a flexible portion 1010 adjacent to the front end portion 110 and a rigid portion 1020 coupled to the flexible portion 1010. The rigid portion 1020 may extend rearwardly from the flexible portion 1010, alternatively, the rigid portion 1020 may wrap at least a portion of the flexible portion 1010 to ensure the local stiffness of the ureteroscope main body 10.

Correspondingly, the operating portion 20 further includes a fifth operating end 26 operatively connected to the flexible portion 1010 and an operating mechanism 28 mounted to the fifth operating end 26. The operating mechanism 28 is operatively connected to the flexible portion 1010 through the fifth operating end 26 to control the bending degree of the flexible portion 1010, so that the ureteroscope main body 10 can reach different target positions, and the bending degree of the flexible portion 1010 can be adjusted according to an actual situation. In an embodiment, the operating mechanism 28 includes a control wire 281 connected to the flexible portion 1010 and a regulator 282 connected to the control wire 281. The regulator 282 is configured to drive the control wire 281 to pull the flexible portion 1010 to bend the flexible portion 1010. The structure of the operating mechanism 28 and the manner of controlling the bending of the flexible portion 1010 are not limited therein, that is, the operating mechanism 28 may be designed as other structures and control the bending of the flexible portion 1010 in other manners.

In an embodiment, at least a part of the front end portion 110 of the ureteroscope main body 10 is the flexible portion 1010, so that the perfusion channel 12 and the suction channel 13 can be bent, and the suction opening 131 and the perfusion opening 121 can face a calculus c at a target position. The flexible portion 1010 includes an active bending portion 1011 and a passive bending portion 1012. The active bending portion 1011 can be bent under the manipulation of the operating portion 20 and maintains a bent state, and the passive bending portion 1012 is bent along with the bending of the active bending portion 1011.

The present application also provides a using method of a break-during-suction type surgical ureteroscope, which includes: S110, a lithotripter extends out and breaks a calculus; S120, the crushed calculus is guided to a suction opening and the crushed calculus at the suction opening is clamped; S130, the lithotripter retracts to the suction opening and breaks the crushed calculus blocked at the suction opening, so that the crushed calculus is discharged out of the body through the suction channel.

The operation process of the break-during-suction type surgical ureteroscope 100 will be described below by taking the application of the break-during-suction type surgical ureteroscope 100 to remove calculus c in the renal pelvis p as an example.

In step S110, the lithotripter 30 extends out and breaks a calculus. Preparation is required prior to breaking the calculus through the lithotripter 30. Specifically, firstly, the tube scope main body 10 may be inserted to an initial predetermined position. Specifically, the ureteroscope main body 10 may enter the kidney along the ureter of the patient and reach an initial predetermined position. In this process, the image of the surroundings where the ureteroscope main body 10 passes can be acquired and displayed by the image acquisition device 300 provided on the ureteroscope main body 10 and the image outputting device 500 communicating with the image acquisition device 300, and cooperating with the guiding mechanism 600 to guide the break-during-suction type surgical ureteroscope 100 to the initial predetermined position. Specifically, the guiding mechanism 600 may enter the perfusion channel 12 through the operating portion 20 and guide the ureteroscope main body 10 to the initial predetermined position. After the ureteroscope main body 10 reaches the initial predetermined position, the guiding mechanism 600 can be removed.

The lithotripter 30 may be placed in the initial predetermined position of the kidney prior to or after inserting the ureteroscope main body 10. Specifically, the lithotripter 30 is provided in the fiber channel 14 and extends or retracts from the suction opening 131.

Then, the flexible portion 1010 is controlled to bend by the operating mechanism 28 of the operating portion 20, so that the suction opening 131 and the perfusion opening 121 can face the calculus c at the target position in the renal pelvis p.

During the process of controlling the bending of the flexible portion 1010 through the operating mechanism 28 of the operating portion 20, the flexible portion 1010 may be controlled to bend at a desired degree of bending according to the target position. When the break-during-suction type surgical ureteroscope 100 is configured to break the calculus c located in the suprarenal pelvis, the flexible portion 1010 is controlled to bend with a first curvature. When the break-during-suction type surgical ureteroscope 100 is configured to break the calculus c located in the renal pelvis, the flexible portion 1010 is controlled to bend with a second curvature. When the break-during-suction type surgical ureteroscope 100 is configured to break the calculus c located in the infrarenal pelvis, the flexible portion 1010 is controlled to bend with a third curvature. The third curvature is greater than the second curvature and the first curvature.

Figure 11A:
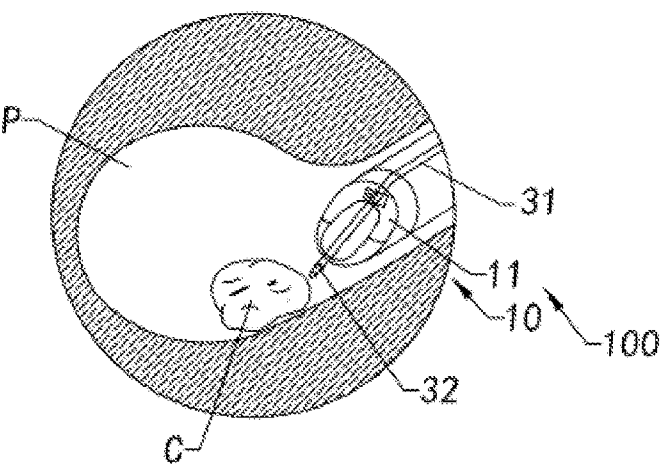
FIG. 11A is a first schematic view of an operation process of the break-during-suction type surgical ureteroscope according to an embodiment of the present application.

In the process of breaking the calculus c by the lithotripter 30, referring to FIG. 11A, the lithotripter 3030 may be extended to the front of the suction opening 131 to break the calculus c at the target position, and the lithotripter 30 may be a holmium laser.

Figure 11B:
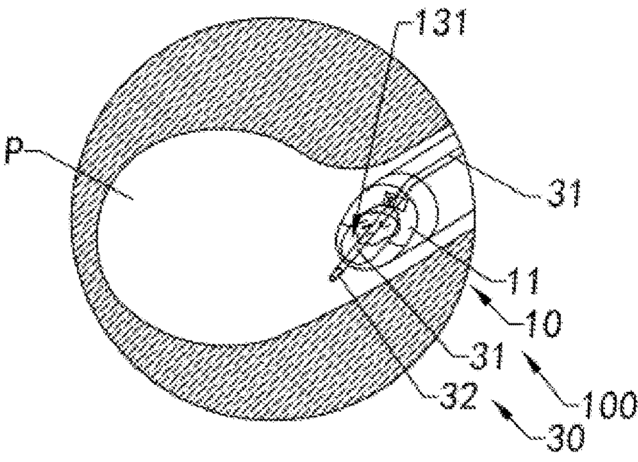
FIG. 11B is a second schematic view of an operation process of the break-during-suction type surgical ureteroscope according to an embodiment of the present application.

In step S120, referring to FIG. 11B, the crushed calculus is guided to the suction opening 131 and the crushed calculus at the suction opening 131 is clamped. Specifically, during the process of breaking the calculus c by the lithotripter 30, or after the calculus c is broken by the lithotripter 30, a fluid may be injected from the perfusion opening 121 of the break-during-suction type surgical ureteroscope 100 to the target position to impact the crushed calculus. Specifically, the fluid may be injected into the perfusion channel 12 through the fluid injection device 700 connected to the operating portion 20, and the fluid may be injected to the target position to impact the crushed calculus.

In the process of impacting crushed calculus, the fluid and the crushed calculus can be sucked by negative pressure suction, the fluid carrying the crushed calculus is diverted under the action of negative pressure suction, renal pelvis p recoil, etc., and flows back to the suction opening 131 of the break-during-suction type surgical ureteroscope 100 capable of circularly removing the crushed calculus in the second direction. That is, during impacting crushed calculus, the fluid is guided to flow back to the suction opening 131 of the break-during-suction type surgical ureteroscope 100 in the second direction. A predetermined angle is formed between the first direction and the second direction. Specifically, the crushed calculus and the fluid may be sucked by the suction device 800 connected to the operating portion 20, so that the fluid and the crushed calculus are discharged through the fluid outlet channel 13 to maintain the pressure in the kidney. During the process of sucking the crushed calculus to the suction opening 131 of the suction channel 13 of the break-during-suction type surgical ureteroscope 100, the suction force to the fluid and the crushed calculus can be adjusted by adjusting the air pressure in the suction channel 13.

In the embodiment of the application, the orientation of the perfusion opening 121 is a first orientation, and the orientation of the suction opening 131 is a second orientation, and the fluid can be injected into the renal pelvis p from the perfusion opening 121 along the perfusion channel 12 in a first direction directed by the first orientation, and is sucked into the suction channel 13 of the break-during-suction type surgical ureteroscope 100 from the suction opening 131 in a second direction directed by the second orientation after being diverted to form a fluid loop.

During the process of guiding the crushed calculus to the suction opening 131, some larger-sized crushed calculus will be clamped at the suction opening 131, causing the suction opening 131 to be blocked. Correspondingly, the lithotripter 30 can crush the crushed calculus or scatter the crushed calculus.

Figure 11C:
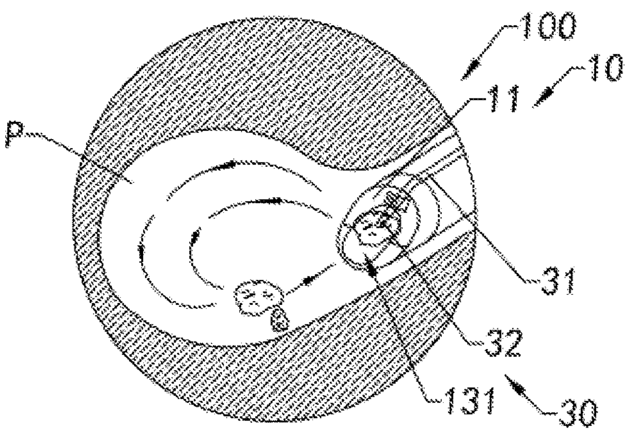
FIG. 11C is a third schematic view of an operation process of the break-during-suction type surgical ureteroscope according to an embodiment of the present application.
Figure 11D:
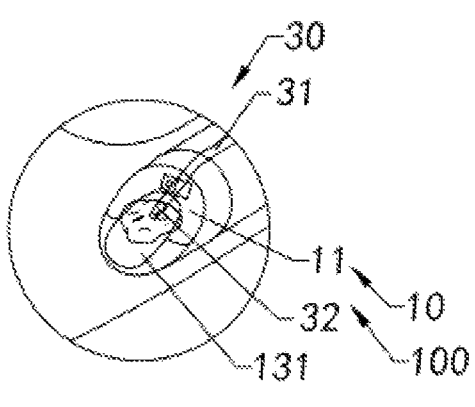
FIG. 11D is a fourth schematic view of an operation process of the break-during-suction type surgical ureteroscope according to an embodiment of the present application.

Correspondingly, in step S130, the lithotripter 30 retracts to the suction opening 131 and breaks the crushed calculus at the suction opening 131, so that the crushed calculus is discharged out of the body through the suction channel 13. Specifically, as shown in FIGS. 11C and 11D, when the crushed calculus is impacted by the fluid or sucked to the suction opening 131 and clamped at the suction opening 131, the lithotripter 30 may be retracted to the suction opening 131 and break the crushed calculus at the suction opening 131, so that the crushed calculus is crushed or even pulverized, so that the crushed calculus can smoothly enter the suction channel 13 from the suction opening 131.

It should be noted that, since the crushed calculus is stuck or clamped at the suction opening 131, the position of the crushed calculus is relatively stable, and the lithotripter 30 can accurately break the crushed calculus at the suction opening 131. In addition, during the process of breaking the crushed calculus by the lithotripter 30, the crushed calculus abuts against the inner peripheral wall of the suction channel 13. When the impact force generated by the lithotripter 30 acts on the crushed calculus, the crushed calculus will receive most of the energy generated by the lithotripter 30, so the crushed calculus is easily crushed.

After lithotripter 30 retracts to the suction opening 131, the calculus stuck in the suction opening 131 can be scattered, so that the calculus that can pass through the suction opening 131 and enter the suction channel 131 from the suction opening 131. In this way, the crushed calculus can be quickly discharged, so as to improve the calculus discharging efficiency. In this way, the lithotripter 30 can not only break the distant calculus c, but also crush or even pulverize the crushed calculus adjacent to the suction opening 131 to prevent the crushed calculus from blocking the suction opening 131 of the suction channel 13.

It should be noted that, during the process of breaking calculus c by the lithotripter 30, the ureteroscope main body 10 can be rotated, so that the lithotripter 30 can break the calculus c in multiple directions, and the fluid injected from the perfusion opening 121 can impact the calculus in all directions.

In conclusion, the break-during-suction type surgical ureteroscope 100 and the method for removing calculus using the ureteroscope according to the embodiments of the present application are illustrated. The break-during-suction type surgical ureteroscope 100 prevents the crushed calculus from being blocked through the break-during-suction type calculus discharging solution, so as to improve the calculus discharging efficiency.

It should be understood by those skilled in the art that the embodiments of the present disclosure described in the above description and drawings are only examples and do not limit the present disclosure. The object of the present disclosure has been fully and effectively achieved. The functional and structural principles of the present disclosure have been described in the embodiments, and the embodiments of the present disclosure may have any variations or modifications without departing from the principles.

What is claimed is:

1. A break-during-suction type surgical ureteroscope, comprising:

a ureteroscope main body having a front end portion and a rear end portion, an operating portion operably coupled to the rear end portion of the ureteroscope main body, and a lithotripter;

wherein the ureteroscope main body comprises a tube structure body, at least one perfusion channel in the tube structure body extending from the rear end portion to the front end portion, the at least one perfusion channel is provided with at least one perfusion opening located at the front end portion; and a suction channel in the tube structure body extending from the front end portion to the rear end portion, the suction channel is provided with a suction opening located at the front end portion;

wherein the lithotripter is movably provided in the tube structure body and is capable of switching between a first state and a second state, when in the first state, a cutting head of the lithotripter extends out of the suction opening and is configured to break calculus, and when in the second state, the cutting head of the lithotripter retracts to the suction opening and is configured to break calculus blocked in the suction opening;

wherein the ureteroscope main body further comprises a crushed calculus channel in communication with the suction channel, the lithotripter is telescopically located in the crushed calculus channel, and when the lithotripter is in the first state, the cutting head extends into the suction channel through the crushed calculus channel to extend out of the suction opening.

2. The break-during-suction type surgical ureteroscope according to claim 1, wherein the crushed calculus channel comprises a main body section and a communication section extending between the main body section and the suction channel, and the communication section is in communication with the suction channel and the main body section.

3. The break-during-suction type surgical ureteroscope according to claim 2, wherein an angle formed between a central axis of the communication section and a central axis of the suction channel ranges from 0° to 45°.

4. The break-during-suction type surgical ureteroscope according to claim 3, wherein when the lithotripter is in the second state, the cutting head of the lithotripter is located in a middle area of the suction opening.

5. The break-during-suction type surgical ureteroscope according to claim 4, wherein when the lithotripter is in the second state, a front end of the cutting head is coplanar with the front end surface.

6. The break-during-suction type surgical ureteroscope according to claim 2, wherein the tube structure body has a front end surface and an outer peripheral surface, the suction opening is formed on the front end surface, and the front end surface of the tube structure body extends obliquely forward from a first side of the outer peripheral surface to a second side opposite to the first side along an axial direction of the ureteroscope main body.

7. The break-during-suction type surgical ureteroscope according to claim 1, wherein the crushed calculus channel is located on a lateral side of the suction channel.

8. The break-during-suction type surgical ureteroscope according to claim 1, wherein the crushed calculus channel extends between the suction channel and the rear end portion of the ureteroscope main body, and the crushed calculus channel is provided with a communication opening in communication with the suction channel and the crushed calculus channel.

9. The break-during-suction type surgical ureteroscope according to claim 1, wherein the operating portion comprises a first operating end in communication with the perfusion channel, a second operating end in communication with the suction channel, and a third operating end in communication with the crushed calculus channel.

10. The break-during-suction type surgical ureteroscope according to claim 1, wherein the perfusion opening of the perfusion channel has a first orientation, so as to allow fluid to be injected into a renal pelvis from the perfusion opening along the perfusion channel in a first direction directed by the first orientation, and the suction opening of the suction channel has a second orientation forming a predetermined angle with the first orientation, so as to allow the fluid to be sucked into the suction channel from the suction opening in a second direction directed by the second orientation after being diverted in the renal pelvis to form a fluid loop.

11. The break-during-suction type surgical ureteroscope according to claim 1, wherein the tube structure body has a front end surface and an outer peripheral surface formed on the front end surface, the perfusion opening is formed on the outer peripheral surface of the tube structure body, and the suction opening is formed on the front end surface of the tube structure body.

* * * * *